US008173847B2

(12) United States Patent
Fischbach et al.

(10) Patent No.: US 8,173,847 B2
(45) Date of Patent: May 8, 2012

(54) METHOD FOR THE PRODUCTION OF ALDEHYDES

(75) Inventors: Andreas Fischbach, Schwindegg (DE); Klaus Schmid, Dinslaken (DE); Christoph Balzarek, Krefeld (DE); Wolfgang Dukat, Oberhausen (DE); Sandra Fürmeier, Körle (DE); Rainer Lukas, Essen (DE); Horst Scholz, Dinslaken (DE); Edgar Storm, Oberhausen (DE)

(73) Assignee: Oxea GmbH, Oberhausen (DE)

( * ) Notice: Subject to any disclaimer, the term of this patent is extended or adjusted under 35 U.S.C. 154(b) by 150 days.

(21) Appl. No.: 12/734,435

(22) PCT Filed: Oct. 28, 2008

(86) PCT No.: PCT/EP2008/009084
§ 371 (c)(1),
(2), (4) Date: Apr. 30, 2010

(87) PCT Pub. No.: WO2009/059713
PCT Pub. Date: May 14, 2009

(65) Prior Publication Data
US 2010/0256422 A1 Oct. 7, 2010

(30) Foreign Application Priority Data
Nov. 9, 2007 (DE) .................. 10 2007 053 385

(51) Int. Cl.
*C07C 45/50* (2006.01)

(52) U.S. Cl. ........................................ 568/451
(58) Field of Classification Search .................. 568/451
See application file for complete search history.

(56) References Cited

U.S. PATENT DOCUMENTS

| 4,148,830 A | 4/1979 | Pruett et al. ............ 260/604 |
| 4,247,486 A | 1/1981 | Brewester et al. ........ 568/454 |
| 4,400,547 A * | 8/1983 | Dawes et al. ............ 568/454 |

FOREIGN PATENT DOCUMENTS

| DE | 1 920 960 | 11/1969 |
| DE | 3822038 A1 | 3/1990 |
| EP | 0 695 734 A1 | 2/1996 |
| GB | 1 202 507 | 8/1970 |

* cited by examiner

*Primary Examiner* — Sikarl Witherspoon
(74) *Attorney, Agent, or Firm* — Michael W. Ferrell

(57) ABSTRACT

Aldehydes are produced by unmodified rhodium catalyzed hydroformylation process in a homogeneous organic phase using a solution of unmodified rhodium catalyst and an organic acid in a total amount, calculated as acid equivalent, of from greater than 3 moles to 3000 moles of acid per mole of rhodium. The organic acid is selected from: saturated aliphatic monocarboxylic acids having from 5 to 13 carbon atoms in the molecule; saturated aliphatic dicarboxylic acids having from 5 to 13 carbon atoms in the molecule; sulphonic acids having from 1 to 12 carbon atoms in the molecule; and combinations thereof. Use of the process can lead to either a significant increase in conversion without reducing selectivity for the desired aldehyde or a reduction in the specific use of rhodium.

43 Claims, No Drawings

METHOD FOR THE PRODUCTION OF ALDEHYDES

CLAIM FOR PRIORITY

This substitute specification is a submitted as a national phase entry of International Patent Application No. PCT/EP2008/009084, filed Oct. 28, 2008, entitled "Method for the Production of Aldehydes" which claims priority to German Patent Application 10 2007 053 385.5, filed Nov. 9, 2007, of the same title. The priorities of International Patent Application No. PCT/EP2008/009084 and German Patent Application 10 2007 053 385.5 are hereby claimed and the referenced priority applications are incorporated herein in their entireties.

BACKGROUND OF THE INVENTION

The present invention relates to a process for preparing aldehydes in the presence of a catalyst based on rhodium and in the absence of complex-forming organophosphorus compounds in a reaction zone, wherein a rhodium-containing organic solution which has been mixed beforehand with at least one organic acid or mixture thereof is fed to the reaction zone.

Hydroformylation or the oxo process is the transition metal-catalysed reaction of olefins or olefinically unsaturated compounds with hydrogen and carbon monoxide to form aldehydes and alcohols which have one more carbon atom than the olefin used. The hydroformylation process has now attained considerable economic and industrial importance. The aldehydes obtained initially in this process are used as such or represent valuable intermediates for the production of, for example, alcohols, carboxylic acids, esters or amines.

Hydroformylation is catalysed by hydridometal carbonyls, preferably those of metals of transition group VIII of the Periodic Table of the Elements. Apart from cobalt, the classic catalyst metal, catalysts based on rhodium have been increasingly used for some years. In contrast to cobalt, rhodium allows the reaction to be carried out at a relatively low pressure. In addition, when terminal olefins are used, straight-chain n-aldehydes are preferentially formed and isoaldehydes are formed to only a minor extent. Finally, the hydrogenation of the feed olefins to saturated hydrocarbons is also significantly lower in the presence of rhodium catalysts than when using cobalt catalysts.

Hydroformylation of olefinically unsaturated compounds is carried out industrially in the presence of rhodium carbonyl complexes with tertiary organic phosphine or phosphite ligands as catalysts. In one process variant, the reaction is carried out in a homogeneous phase, i.e. feed olefin, catalyst and reaction products are present together in solution. The reaction products are usually separated off from the mixture by distillation, more rarely by other processes such as extraction. The hydroformylation process carried out in the homogeneous phase can be in the form of a gas recycle process as described in U.S. Pat. No. 4,247,486 or in the form of a liquid recycle process as described in U.S. Pat. No. 4,148,830.

In a further process variant, the rhodium-catalysed hydroformylation reaction can also be carried out in the absence of complex-forming ligands, for example phosphines or phosphites. Such rhodium catalysts which have not been modified with phosphines or phosphites and their suitability for hydroformylation catalysts are known from the literature and they are referred to as unmodified rhodium catalysts. It is assumed in the technical literature that the rhodium compound $HRh(CO)_4$ is the catalytically active rhodium species in hydroformylation using unmodified rhodium catalysts, although this has not been conclusively proven because of the many mechanisms proceeding simultaneously in the reaction zone. The unmodified rhodium catalysts are formed from rhodium compounds, for example rhodium salts such as rhodium(III) chloride, rhodium(III) nitrate, rhodium(III) acetate, rhodium (II) acetate, rhodium(III) sulphate or rhodium(III) ammonium chloride, from rhodium chalcogenides such as rhodium (III) oxide or rhodium(III) sulphide, from salts of rhodium oxo acids, for example rhodates, from rhodium carbonyl compounds such as $Rh_4(CO)_{12}$ and $Rh_6(CO)_{16}$ or from organorhodium compounds such as rhodium carbonyl acetonylacetonate, cyclooctadiene rhodium acetate or chloride in the presence of carbon monoxide/hydrogen mixtures, also referred to as synthesis gas, in the reaction zone under the conditions of the hydroformylation reaction. Here, the rhodium compound can be used as solid or advantageously in solution. Hydroformylation processes carried out in the presence of unmodified rhodium complexes are known, for example, from DE 38 22 038 A1, in which rhodium 2-ethylhexanoate is used, or from EP 0 695 734 A1, according to which a solution of a previously formed rhodium carbonyl compound in the olefinically unsaturated compound to be reacted is used.

Owing to the absence of stabilizing ligands, precipitation of metallic rhodium from the crude hydroformylation mixture obtained by the unmodified process variant and taken from the reaction zone can occur during the work-up of the mixture by distillation. The rhodium precipitated in the work-up apparatus for the crude hydroformylation mixture cannot be recirculated to the hydroformylation process and therefore leads to rhodium losses which, owing to the high prices of noble metal, represent an economic disadvantage. To reduce rhodium losses in the work-up stage of a crude hydroformylation mixture which has been obtained by unmodified rhodium-catalysed hydroformylation, EP 0 695 734 A1 proposes firstly carrying out an extraction with an aqueous solution of a water-soluble phosphorus-containing complexing agent, with rhodium being extracted into the aqueous phase and aldehyde or alcohol being isolated from the remaining hydroformylation mixture. The aqueous extract is subsequently treated with an organic liquid in the presence of carbon monoxide or gases containing carbon monoxide under superatmospheric pressure at elevated temperature, resulting in rhodium going as rhodium carbonyl into the organic phase which can subsequently be recirculated to the reaction zone.

Apart from the rhodium precipitates which can occur in the work-up of a crude hydroformylation mixture obtained by unmodified rhodium catalysis, precipitation of rhodium metal close to the inlet region can also be expected when the rhodium-containing solution is introduced into the reaction zone. This precipitated rhodium metal is no longer converted into catalytically active rhodium carbonyl in the reaction zone, even under synthesis gas pressure. As a result, there is firstly only a smaller amount, based on the rhodium used, of catalytically active rhodium available and, secondly, the precipitated rhodium metal remains in the reaction zone and leads to rhodium losses. According to DE 19 20 960 A1, heating of the rhodium solution and of the mixture of olefinically unsaturated compound and rhodium solution in the absence of carbon monoxide has to be avoided in a continuously operated, unmodified hydroformylation process. Likewise, no high rhodium concentrations should occur during mixing of the rhodium solution with the olefinically unsaturated compound in the reaction zone. DE 19 20 960 A1 therefore recommends intimately mixing synthesis gas, the olefinically unsaturated compound and the rhodium solution in the vicinity of the inlet into the reaction zone. Here, a solution of rhodium compound, for example rhodium chloride or nitrate, in a polar organic solvent is fed to the reaction zone, with the rhodium compound preferably being insoluble in the olefinically unsaturated compound. For example, use is made of a solution of rhodium acetate in a mixture of methanol and acetic acid, in acetic acid or in propionic acid. The known continuously operated hydroformylation process allows conversions of 1-octene of 94-96% at a residence time of about 2 hours and a rhodium concentration of 14 ppm, with rhodium precipitates in the vicinity of the inlet for the rhodium solution into the reaction zone being able to be reduced at the same time. It is likewise pointed out that the rhodium compound added should be insoluble or virtually insoluble in the olefinically unsaturated compound in order to avoid high rhodium concentrations during mixing of the rhodium solution with the olefinically unsaturated compound. If locally high rhodium concentrations occur, precipitation of rhodium metal can occur in the presence of the olefinically unsaturated compound.

DETAILED DESCRIPTION OF THE INVENTION

The invention is described in detail below by reference to the various examples. Such discussion is for purposes of illustration only. Modifications to particular examples within the spirit and scope of the present invention, set forth in the appended claims, will be readily apparent to one of skill in the art. Terminology used herein is given its ordinary meaning unless otherwise stated herein.

It has surprisingly been found that targeted addition of an organic acid to a rhodium-containing organic solution which is subsequently fed to the reaction zone in an unmodified rhodium-catalysed hydroformylation process leads to a significant increase in conversion without the selectivity being reduced, so that the yield of the desired aldehyde compound can be increased by the targeted addition of acid. If, on the other hand, the absolute output of the desired aldehyde is to remain constant because of the plant design or because of market circumstances, the mode of operation according to the invention allows the specific use of rhodium, based on the amount of aldehyde produced, to be reduced, which is a considerable economic advantage.

The invention therefore provides a process for preparing aldehydes by introduction of an organic solution containing at least one rhodium compound in dissolved form into a reaction zone and reaction of olefinically unsaturated compounds with carbon monoxide and hydrogen in a homogeneous organic phase in the presence of at least one rhodium compound and in the absence of complex-forming organophosphorus compounds in this reaction zone. It is characterized in that at least one organic acid selected from among saturated aliphatic monocarboxylic acids having from 5 to 13 carbon atoms in the molecule, saturated aliphatic dicarboxylic acids having from 5 to 13 carbon atoms in the molecule and sulphonic acids having from 1 to 12 carbon atoms in the molecules or mixture thereof in a total amount, calculated as acid equivalent, of from >3 mol to 3000 mol per mole of rhodium is added to the rhodium-containing organic solution and this solution is subsequently fed to the reaction zone.

The organic solution containing at least one rhodium compound in dissolved form which is fed to the reaction zone will hereinafter also be referred to as rhodium solution. The solvents used for preparing this rhodium solution have to ensure complete dissolution of the rhodium compound. Suitable solvents are, for example, water-insoluble ketones, dialkyl ethers, aliphatic nitriles, aromatic hydrocarbons such as benzene or toluene, the isomeric xylenes or mesitylene, saturated cycloaliphatic hydrocarbons such as cyclopentane or cyclohexane or saturated aliphatic hydrocarbons such as n-hexane, n-heptane or n-octane. Polar solvents such as aliphatic saturated monoalcohols, for example methanol, ethanol, propanol, n-butanol and isobutanol, the isomeric pentanols, 2-ethylhexanol, isononanol based on 3,5,5-trimethylhexanol, saturated polyhydric alcohols such as 1,3-propanediol, 1,4-butanediol or polyalkylene glycols, such as ethylene glycol, triethylene glycol and their monoethers and diethers, for example their methyl or butyl ethers, or polar ester compounds such as Texanol® from Eastman are also suitable. Mixtures of solvents can also be used as long as sufficient solubility of the rhodium compound is ensured and the solvent or the solvent mixture is inert under the subsequent hydroformylation conditions. 2-Ethylhexanol and toluene have been found to be particularly useful as solvents for preparing the rhodium solution.

As rhodium compounds used for preparing the rhodium solution, use is made of salts of aliphatic monocarboxylic or polycarboxylic acids having from 2 to 13, preferably from 7 to 11, carbon atoms in the molecule. Suitable rhodium salts are rhodium acetate, rhodium propionate, rhodium oxalate, rhodium malonate, rhodium 2-ethylhexanoate, rhodium isononanoate, with the isononanoic acid being prepared by hydroformylation of diisobutylene with subsequent oxidation of the hydroformylation product, or rhodium isotridecanoate, with the isotridecanoic acid being prepared by hydroformylation of tetrapropylene and subsequent oxidation of the hydroformylation product. Furthermore, carbonyl compounds of rhodium, e.g. tricarbonylrhodium $Rh(CO)_3$, tetracarbonylrhodium $[Rh(CO)_4]_2$, dodecacarbonyl-tetrarhodium $Rh_4(CO)_{12}$, have been found to be very useful. Although halogen carbonyl compounds such as dicarbonylrhodium bromide $[Rh(CO)_2]Br$, and dicarbonylrhodium iodide $[Rh(CO)_2]I$ can also be used, they are employed to only a limited extent because of the corrosion behaviour of the halide ions. Finally, complexes of rhodium, in particular rhodium(III) compounds, are also suitable starting materials for preparing the catalytically active metal component in the catalyst system. These compounds contain monodentate, bidentate or tridentate ligands such as β-diketones, e.g. acetylacetone, or aliphatic or cycloaliphatic and diethylenically unsaturated hydrocarbons such as cyclopentadiene and 1,5-cyclooctadiene. Rhodium compounds which are particularly suitable for preparing the rhodium solution are rhodium oxides, rhodium carbonyls, rhodium acetate, rhodium 2-ethylhexanoate, rhodium isononanoate and rhodium(III) acetylacetonate.

The preparation of the rhodium solution from the rhodium compound and the solvent or solvent mixture is carried out in a conventional fashion, for example by simple dissolution of the fresh rhodium compound, with the exclusion of oxygen being advisable. In addition, it is also possible to use rhodium solutions which are obtained in the recycling of used rhodium catalysts. Such rhodium-containing organic solutions in which rhodium carboxylates are present in dissolved form can be obtained by the methods described in DE 36 26 536 A1 or DE 38 33 427 A1. Here, an aqueous rhodium solution is firstly oxidized in the presence of a carboxylate or a mixture of a carboxylate and a carboxylic acid, for example 2-ethylhexanoic acid. Rhodium is obtained as water-insoluble carboxylate which can be extracted into the organic phase by means of a water-insoluble solvent, for example toluene. It can be assumed that the carboxylic acid present in the preceding oxidation step also dissolves in the organic solvent. The rhodium solutions obtained as described in DE 36 26 536 A1 and DE 38 33 427 A1 therefore already have a certain carboxylic acid content and, according to the prior art, are used without after-treatment as catalyst constituent for the hydroformylation reaction.

It has surprisingly been found that, in the case of rhodium solutions which already contain a certain amount of a carboxylic acid in dissolved form, the active addition of an organic acid has an advantageous effect on the aldehyde yield in the subsequent hydroformylation reaction. According to the invention, at least one organic acid is added to the rhodium solution in such an amount that from >3 moles to 3000 moles, preferably from 50 to 2000 moles and in particular from 100 to 1000 moles, of organic acid, calculated as acid equivalent, are present per mole of rhodium. Based on the amount of rhodium, the targeted addition of an organic acid can surprisingly be varied over a wide range without appreciable formation of undesirable by-products, for example high boilers, occurring. However, if the critical molar ratio is exceeded, the acid content of the reaction mixture becomes too high, so that secondary reactions with the aldehydes already formed have to be expected. An excessively high addition of acid likewise makes the hydroformylation process unnecessarily expensive. On the other hand, if the molar ratio of rhodium to organic acid is below the critical value, an advantageous effect on the aldehyde yield is no longer observed. The addition of the organic acid to the rhodium solution is generally carried out at room temperature under conventional conditions. It is possible to work with exclusion of oxygen, but this is not absolutely necessary.

Suitable organic acids are saturated aliphatic monocarboxylic and dicarboxylic acids having from 5 to 13, preferably from 5 to 11, carbon atoms in the molecule. For example, it is possible to add n-valeric acid, 2-methylbutyric acid, 2-ethylhexanoic acid, isononanoic acid prepared by hydroformylation of diisobutylene and subsequent oxidation of the hydroformylation product or isotridecanoic acid prepared by hydroformylation of tetrapropylene and subsequent oxidation of the hydroformylation product to the required content. A suitable aliphatic dicarboxylic acid which can be added is adipic acid. Organic acids which can be used successfully in the process of the invention likewise include sulphonic acids having from 1 to 12 carbon atoms in the molecule, in particular aliphatic, cycloaliphatic, aromatic and/or aralipathic sulphonic acids, for example methanesulphonic acid, para-toluenesulphonic acid, benzenesulphonic acid or benzenedisulphonic acid. The addition of branched saturated aliphatic monocarboxylic acids such as 2-ethylhexanoic acid or isononanoic acid has been found to be particularly useful in the preparation of the rhodium solution. Mixtures of organic acids, for example mixtures of 2-ethylhexanoic acid and isononanoic acid, can also be used. When a mixture of organic acids is added to the rhodium solution to the desired content, the abovementioned molar ratio of rhodium to organic acid is based on the total content of organic acids added, calculated as acid equivalent.

The rhodium concentration in the rhodium solution which is, after addition of the organic acid, fed to the reaction zone is relatively high compared to the concentration in the reaction zone itself in which the hydroformylation reaction takes place and is generally from 100 to 10 000 ppm, preferably from 1000 to 10,000 ppm. After introduction of the rhodium solution into the reaction zone, the rhodium concentration is reduced to a content of from 1 to 100 ppm as a result of dilution in the olefinically unsaturated compound added and in any solvent which may be present in the hydroformylation stage. The actual active hydroformylation catalyst is then formed from the rhodium compound dissolved in the rhodium solution introduced in the presence of synthesis gas under the conditions prevailing in the reaction zone.

The hydroformylation process of the invention is carried out in a homogeneous organic phase in the presence of at least one rhodium compound and in the absence of organophosphorus complex-forming compounds. Such rhodium catalysts which, for example, have not been modified with phosphines or phosphites and their suitability as catalysts for hydroformylation are known from the literature and they are referred to as unmodified rhodium catalysts. In the technical literature, it is assumed that the rhodium compound $HRh(CO)_4$ is the catalytically active rhodium species in hydroformylation using unmodified rhodium catalysts. Since the use of rhodium catalysts which have not been modified with phosphines generally requires a lower rhodium content, a rhodium content of from 1 to 100 ppm, preferably from 2 to 30 ppm, based on the homogeneous reaction mixture, is generally employed.

The expression "homogeneous organic phase" refers to a homogeneous solution composed essentially of the solvent, if added in the hydroformylation stage, the catalyst comprising the rhodium compound dissolved in the rhodium solution introduced including the solvent present and the added organic acid, the unreacted olefinically unsaturated starting compound, the aldehyde formed and the by-products formed. If appropriate, addition of a solvent in the hydroformylation stage can prove to be advantageous. Solvents used for the hydroformylation reaction are organic compounds in which the starting material, including the rhodium compound, the solvent and the organic acid introduced via the rhodium solution, reaction product and catalyst are soluble. Examples of such solvents are aromatic hydrocarbons such as benzene and toluene or the isomeric xylenes and mesitylene. Other solvents which can be used are paraffin oil, cyclohexane, n-hexane, n-heptane or n-octane, ethers such as tetrahydrofuran, ketones or Texanol® from Eastman. The proportion of solvent in the reaction medium can be varied over a wide range and is usually from 10 to 80% by weight, preferably from 20 to 50% by weight, based on the reaction mixture.

The reaction of the olefins or the olefinically unsaturated compounds with hydrogen and carbon monoxide to form aldehydes is carried out at temperatures of from 20 to 180° C., preferably from 50 to 150° C. and in particular from 100 to 150° C., and pressures of from 0.1 to 70 MPa, preferably from 0.1 to 60 MPa and in particular from 0.1 to 30 MPa. The reaction conditions to be employed in a particular case also depend on the type of olefinically unsaturated compound to be reacted. Thus, reactive starting materials can be reacted at relatively low temperatures and pressures and in the presence of small amounts of catalyst, while less reactive compounds require correspondingly more severe reaction conditions.

The composition of the synthesis gas, i.e. the proportions of carbon monoxide and hydrogen in the gas mixture, can be varied within wide limits. In general, mixtures in which the molar ratio of carbon monoxide to water is from 5:1 to 1:5 are used. This ratio is usually 1:1 or deviates only slightly from this value. The olefinic compound can be introduced into the reaction zone as such or in solution. Suitable solvents are ketones such as acetone, methyl ethyl ketone, aceto-phenone, lower aliphatic nitriles such as acetonitrile, propionitrile or benzonitrile, dimethylformamide, linear or branched saturated aliphatic monohydroxy compounds such as methanol, ethanol, propanol and isopropanol, aromatic hydrocarbons such as benzene or toluene and saturated cycloaliphatic hydrocarbons such as cyclopentane or cyclohexane.

The process of the invention can be carried out either batchwise or continuously. The desired aldehydes are isolated from the crude hydroformylation product by conventional methods, for example by distillation. Aldehyde and further volatile components are taken off as overhead product and, if required, subjected to a further fine purification. The rhodium used remains in the distillation residue and is recovered by known methods.

The use of the novel process is not restricted to particular olefinically unsaturated compounds as starting materials. The olefinically unsaturated compound can have one or more carbon-carbon double bond(s). The carbon-carbon double bond can be terminal or internal (internal olefins). Preference is given to olefinically unsaturated compounds having a terminal carbon-carbon double bond or cyclic olefinically unsaturated compounds having unsubstituted double bonds.

Examples of α-olefinic compounds (having a terminal carbon-carbon double bond) are alkenes, alkenyl alkanoates, alkenyl alkyl ethers and alkenols, in particular those having from 2 to 12 carbon atoms. Without making any claim as to completeness, α-olefinic compounds which may be mentioned are ethylene, propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, allyl chloride, 1,4-hexadiene, 1,3-butadiene, 1,7-octadiene, 3-cyclohexyl-1-butene, hex-1-en-4-ol, oct-1-en-4-ol, vinylcyclohexene, n-propyl 7-octenoate, 7-octenoic acid, 5-hexenamide.

As examples of further suitable olefinic compounds, mention may be made of 2-butene, diisobutylene, tripropylene, raffinate II (mixture of 1-butene, 2-butene and butane), octol or dimersol (dimerization products of butenes), tetrapropylene, cyclohexene, dicyclopentadiene, acyclic, cyclic or bicyclic terpenes such as myrcene, limonene and pinene. The hydroformylation is preferably carried out using olefinically unsaturated compounds having from 2 to 12 carbon atoms in the molecule.

The process of the invention is illustrated below with the aid of a few examples but is not restricted to the embodiments described.

EXAMPLES

General Method

In a 1 L stainless steel autoclave, 300 g of olefin (in these Examples cyclohexene or 1-hexene) were heated to 130° C. over a period of 30 minutes and pressurized with synthesis gas (molar ratio of $CO/H_2$=1:1) to a pressure of 23 MPa. After the reaction temperature had been reached, the rhodium solution which had previously been introduced into an external reservoir was spontaneously pushed into the autoclave by means of a synthesis gas differential pressure of 3 MPa. The hydroformylation was carried out at 130° C. and 26 MPa for at least 2 hours. Samples were taken after 30 and 60 minutes and analysed by gas chromatography. After a reaction time of 120 minutes, the conversions of cyclohexene or 1-hexene were above 98%.

Example 1

Comparative Example

Hydroformylation of Cyclohexene

Using the general experimental method, cyclohexene was reacted in the presence of 3 ppm of rhodium in the form of rhodium 2-ethylhexanoate. The rhodium solution in 2-ethylhexanol as solvent which was introduced into the external reservoir had a molar ratio of rhodium to 2-ethylhexanoic acid of 1:3. Further 2-ethylhexanoic acid was not added to the rhodium solution before introduction into the autoclave. After 60 minutes, the cyclohexene conversion determined by gas chromatography was 70.4%. The selectivity to formylcyclohexane determined by gas chromatography was 94.7%, corresponding to a yield of 66.7%, determined by gas chromatography.

The specific catalyst activity was 26.47 mol of olefin·(mmol of Rh·h)$^{-1}$. This value can be taken as reference value and assigned a relative value of "100".

Example 2

Hydroformylation of Cyclohexene with Addition of 2-Ethylhexanoic Acid

Using the general experimental method, cyclohexene was reacted in the presence of 3 ppm of rhodium in the form of rhodium 2-ethylhexanoate. The rhodium solution in 2-ethylhexanol as solvent which was introduced into the external reservoir was brought to a molar ratio of rhodium to 2-ethylhexanoic acid of 1:125 by addition of 2-ethylhexanoic acid before introduction into the autoclave. After 60 minutes, the cyclohexene conversion determined by gas chromatography was 72.0%. The selectivity to formylcyclohexane determined by gas chromatography was 95.7%, corresponding to a yield of 68.9%, determined by gas chromatography.

The specific catalyst activity was 27.07 mol of olefin·(mmol of Rh·h)$^{-1}$, corresponding to an increase by 2.3 percentage points, based on the reference value.

Example 3

Hydroformylation of Cyclohexene with Addition of 2-Ethylhexanoic Acid

Using the general experimental method, cyclohexene was reacted in the presence of 3 ppm of rhodium in the form of rhodium 2-ethylhexanoate. The rhodium solution in 2-ethylhexanol as solvent which was introduced into the external reservoir was brought to a molar ratio of rhodium to 2-ethylhexanoic acid of 1:2877 by addition of 2-ethylhexanoic acid before introduction into the autoclave. After 60 minutes, the cyclohexene conversion determined by gas chromatography was 78.9%. The selectivity to formylcyclohexane determined by gas chromatography was 95.9%, corresponding to a yield of 75.7%, determined by gas chromatography.

The specific catalyst activity was 29.67 mol of olefin·(mmol of Rh·h)$^{-1}$, corresponding to an increase by 12.1 percentage points, based on the reference value.

Example 4

Hydroformylation of 1-Hexene with Addition of 2-Ethylhexanoic Acid

Using the general experimental method, 1-hexene was reacted in the presence of 3 ppm of rhodium in the form of rhodium 2-ethylhexanoate. The rhodium solution in 2-ethylhexanol as solvent which was introduced into the external reservoir was brought to a molar ratio of rhodium to 2-ethylhexanoic acid of 1:125 by addition of 2-ethylhexanoic acid before introduction into the autoclave. After 30 minutes, the 1-hexene conversion determined by gas chromatography was 57.1%. The aldehyde selectivity to n/i-heptanal determined by gas chromatography was 62.3%, corresponding to a yield of n/i-heptanals of 35.6%, determined by gas chromatography.

The specific catalyst activity was 20.94 mol of olefin·(mmol of Rh·h)$^{-1}$. This value can be taken as reference value and assigned a relative value of "100".

Example 5

Hydroformylation of 1-Hexene with Addition of 2-Ethylhexanoic Acid

Using the general experimental method, 1-hexene was reacted in the presence of 3 ppm of rhodium in the form of rhodium 2-ethylhexanoate. The rhodium solution in 2-ethylhexanol as solvent which was introduced into the external reservoir was brought to a molar ratio of rhodium to 2-ethylhexanoic acid of 1:2877 by addition of 2-ethylhexanoic acid before introduction into the autoclave. After 30 minutes, the 1-hexene conversion determined by gas chromatography was 60.7%. The aldehyde selectivity to n/i-heptanal determined by gas chromatography was 67.3%, corresponding to a yield of n/i-heptanals of 39.3%, determined by gas chromatography.

The specific catalyst activity was 22.26 mol of olefin·(mmol of Rh·h)$^{-1}$, corresponding to an increase by 6.3 percentage points, based on the reference value.

As the examples according to the invention demonstrate, a targeted addition of 2-ethylhexanoic acid to the rhodium solution fed to the reaction zone surprisingly enables both the conversion of olefinically unsaturated compound and the selectivity to the desired aldehydes in the hydroformylation reaction to be increased, so that an overall improvement in the aldehyde yield is achieved. On the other hand, if the absolute aldehyde output is to remain the same, the specific rhodium usage can be reduced in the process of the invention.

Despite the addition of comparatively large amounts of acid, no conspicuously large formation of high boilers during the hydroformylation reaction is observed.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention which is set forth in the claims of this case.

The invention claimed is:

1. An improved process for preparing aldehydes in a homogeneous organic phase in the presence of at least one rhodium compound and in the absence of complex-forming organophosphorus compounds in this reaction zone by:
   a. introduction of an organic solution containing at least one rhodium compound in dissolved form into a reaction zone; and
   b. reaction of olefinically unsaturated compounds with carbon monoxide and hydrogen,
   wherein the improvement comprises:
   addition of at least one organic acid in a total amount, calculated as acid equivalent, of from greater than 3 mol to 3000 mol per mole of rhodium to the rhodium-containing organic solution and subsequent feeding of this solution to the reaction zone, said organic acid being selected from among:
   saturated aliphatic monocarboxylic acids having from 5 to 13 carbon atoms in the molecule;
   saturated aliphatic dicarboxylic acids having from 5 to 13 carbon atoms in the molecule;
   sulphonic acids having from 1 to 12 carbon atoms in the molecule; and combinations thereof.

2. The improved process according to claim 1, wherein the organic acid is a saturated aliphatic monocarboxylic acid selected from the group consisting of:
   (a) n-valeric acid;
   (b) 2-methylbutyric acid;
   (c) 2-ethylhexanoic acid;
   (d) isononanoic acid prepared by hydroformylation of diisobutylene and subsequent oxidation of the hydroformylation product;
   (e) isotridecanoic acid prepared by hydroformylation of tetrapropylene and subsequent oxidation of the hydroformylation product; and
   (f) combinations of any of (a)-(e).

3. The improved process according to claim 1, wherein the organic acid is adipic acid.

4. The improved process according to claim 1, wherein the organic acid is a sulphonic acid, selected from the group consisting of:
   (a) aliphatic;
   (b) cycloaliphatic;
   (c) aromatic;
   (d) araliphatic sulphonic acids; and
   (e) combinations of any of (a)-(d).

5. The improved process according to claim 1, wherein the organic acid is selected from the group consisting of:
   (a) methanesulphonic acid,
   (b) para-toluenesulphonic acid,
   (c) benzenesulphonic acid;
   (d) benzenedisulphonic acid; and
   (e) combinations of any of (a)-(d).

6. The improved process according to claim 1, wherein the solvent in the organic solution containing at least one rhodium compound in dissolved form is selected from the group consisting of 2-ethylhexanol; isononanol based on 3,5,5-trimethylhexanol and combinations thereof.

7. The improved process according to claim 1, wherein the concentration of rhodium in the reaction zone is from 1 to 100 ppm, based on the homogeneous reaction mixture.

8. The improved process according to claim 1, wherein the concentration of rhodium in the reaction zone is from 2 to 30 ppm based on the homogeneous reaction mixture.

9. The improved process according to claim 1, wherein the olefinically unsaturated compounds contain from 2 to 12 carbon atoms in the molecule.

10. The improved process according to claim 1, wherein the reaction of the olefinically unsaturated compounds with carbon monoxide and hydrogen in the reaction zone is carried out at a temperatures of from 20 to 180° C., and a pressure of from 0.1 to 70 MPa.

11. The improved process according to claim 1, wherein the reaction of the olefinically unsaturated compounds with carbon monoxide and hydrogen in the reaction zone is carried out at a temperature of from 50 to 150° C. and a pressure of from 0.1 to 60 MPa.

12. The improved process according to claim 1, wherein the reaction of the olefinically unsaturated compounds with carbon monoxide and hydrogen in the reaction zone is carried out at a temperature of from 100 to 150° C., and a pressure of from 0.1 to 30 MPa.

13. The improved process according to claim 1, wherein the organic solution containing at least one rhodium compound in dissolved form consists essentially of from 50 moles to 2000 moles of acid, in a total amount calculated as acid equivalent, per mole of rhodium.

14. The improved process according to claim 13, wherein the organic acid is a saturated aliphatic monocarboxylic acid selected from the group consisting of:
(a) n-valeric acid;
(b) 2-methylbutyric acid;
(c) 2-ethylhexanoic acid;
(d) isononanoic acid prepared by hydroformylation of diisobutylene and subsequent oxidation of the hydroformylation product; (e) isotridecanoic acid prepared by hydroformylation of tetrapropylene and subsequent oxidation of the hydroformylation product; and
(e) combinations of any of (a)-(d).

15. The improved process according to claim 13, wherein the organic acid is adipic acid.

16. The improved process according to claim 13, wherein the organic acid is a sulphonic acid, selected from the group consisting of:
(a) aliphatic,
(b) cycloaliphatic,
(c) aromatic;
(d) araliphatic sulphonic acids; and
(e) combinations of any of (a)-(d).

17. Process according to claim 13, wherein the organic acid is a sulphonic acid, selected from the group consisting of:
(a) methanesulphonic acid,
(b) para-toluenesulphonic acid,
(c) benzenesulphonic acid;
(d) benzenedisulphonic acid; and
(e) combinations of any of (a)-(d).

18. The improved process according to claim 13, wherein the concentration of rhodium in the reaction zone is from 1 to 100 ppm, based on the homogeneous reaction mixture.

19. The improved process according to claim 13, wherein the concentration of rhodium in the reaction zone is from 2 to 30 ppm based on the homogeneous reaction mixture.

20. The improved process according to claim 13, wherein the olefinically unsaturated compounds contain from 2 to 12 carbon atoms in the molecule.

21. The improved process according to claim 13, wherein the reaction of the olefinically unsaturated compounds with carbon monoxide and hydrogen in the reaction zone is carried out at a temperatures of from 20 to 180° C., and a pressure of from 0.1 to 70 MPa.

22. The improved process according to claim 13, wherein the reaction of the olefinically unsaturated compounds with carbon monoxide and hydrogen in the reaction zone is carried out at a temperature of from 50 to 150° C. and a pressure of from 0.1 to 60 MPa.

23. The improved process according to claim 13, wherein the reaction of the olefinically unsaturated compounds with carbon monoxide and hydrogen in the reaction zone is carried out at a temperature of from 100 to 150° C., and a pressure of from 0.1 to 30 MPa.

24. The improved process according to claim 13, wherein the organic solution containing at least one rhodium compound in dissolved form consists essentially of from 100 moles to 1000 moles organic acid in a total amount calculated as acid equivalent per mole of rhodium.

25. The improved process according to claim 24, wherein the organic acid is a saturated aliphatic monocarboxylic acid selected from the group consisting of:
(a) n-valeric acid;
(b) 2-methylbutyric acid;
(c) 2-ethylhexanoic acid;
(d) isononanoic acid prepared by hydroformylation of diisobutylene and subsequent oxidation of the hydroformylation product;
(e) isotridecanoic acid prepared by hydroformylation of tetrapropylene and subsequent oxidation of the hydroformylation product; and
(f) combinations of any of (a)-(e).

26. The improved process according to claim 24, wherein the organic acid is adipic acid.

27. The improved process according to claim 24, wherein the organic acid is a sulphonic acid, selected from the group consisting of:
(a) aliphatic,
(b) cycloaliphatic,
(c) aromatic;
(d) araliphatic sulphonic acids; and
(e) combinations of any of (a)-(d).

28. The improved process according to claim 24, wherein the organic acid is selected from the group consisting of:
(a) methanesulphonic acid,
(b) para-toluenesulphonic acid,
(c) benzenesulphonic acid;
(d) benzenedisulphonic acid; and
(e) combinations of any of (a)-(d).

29. The improved process according to claim 24, wherein the concentration of rhodium in the reaction zone is from 1 to 100 ppm, based on the homogeneous reaction mixture.

30. The improved process according to claim 24, wherein the concentration of rhodium in the reaction zone is from 2 to 30 ppm based on the homogeneous reaction mixture.

31. The improved process according to claim 24, wherein the olefinically unsaturated compounds contain from 2 to 12 carbon atoms in the molecule.

32. The improved process according to claim 24, wherein the reaction of the olefinically unsaturated compounds with carbon monoxide and hydrogen in the reaction zone is carried out at a temperatures of from 20 to 180° C., and a pressure of from 0.1 to 70 MPa.

33. The improved process according to claim 24, wherein the reaction of the olefinically unsaturated compounds with carbon monoxide and hydrogen in the reaction zone is carried out at a temperature of from 50 to 150° C. and a pressure of from 0.1 to 60 MPa.

34. The improved process according to claim 24, wherein the reaction of the olefinically unsaturated compounds with carbon monoxide and hydrogen in the reaction zone is carried out at a temperature of from 100 to 150° C., and a pressure of from 0.1 to 30 MPa.

35. An improved process for preparing aldehydes in a homogeneous organic phase in the presence of at least one rhodium compound and in the absence of complex-forming organophosphorus compounds in this reaction zone by:
a. introduction of an organic solution containing at least one rhodium compound in dissolved form into a reaction zone; and
b. reaction of olefinically unsaturated compounds with carbon monoxide and hydrogen,
wherein the improvement comprises:
addition of at least one organic acid in a total amount, calculated as acid equivalent, of from greater than 3 mol to 3000 mol per mole of rhodium to the rhodium-containing organic solution and subsequent feeding of this solution to the reaction zone, said organic acid being selected from the group consisting of:
(a) n-valeric acid;
(b) 2-methylbutyric acid;
(c) 2-ethylhexanoic acid;
(d) isononanoic acid prepared by hydroformylation of diisobutylene and subsequent oxidation of the hydroformylation product;

(e) isotridecanoic acid prepared by hydroformylation of tetrapropylene and subsequent oxidation of the hydroformylation product;
(f) methanesulphonic acid,
(g) para-toluenesulphonic acid,
(h) benzenesulphonic acid;
(i) benzenedisulphonic acid;
(j) adipic acid and
(k) combinations of any of (a)-(j).

36. The improved process according to claim 35, wherein the rhodium content of the rhodium-containing organic solution fed to the reaction zone is from 1000 to 10 000 ppm.

37. The improved process according to claim 35, wherein the rhodium content of the rhodium-containing organic solution fed to the reaction zone is from 100 to 10 000 ppm.

38. The improved process according to claim 37, wherein the solvent in the organic solution containing at least one rhodium compound in dissolved form is selected from the group consisting of 2-ethylhexanol; isononanol based on 3,5,5-trimethylhexanol or combinations thereof.

39. The improved process according to claim 38, characterized in that the reaction of the olefinically unsaturated compounds with carbon monoxide and hydrogen in the reaction zone is carried out at a rhodium content of from 1 to 100 ppm, based on the homogeneous reaction mixture.

40. The improved process according to claim 38, characterized in that the reaction of the olefinically unsaturated compounds with carbon monoxide and hydrogen in the reaction zone is carried out at a rhodium content of from 2 to 30 ppm, based on the homogeneous reaction mixture.

41. The improved process according to claim 35, characterized in that the reaction of the olefinically unsaturated compounds with carbon monoxide and hydrogen in the reaction zone is carried out at a rhodium content of from 1 to 100 ppm, based on the homogeneous reaction mixture.

42. The improved process according to claim 35, characterized in that the reaction of the olefinically unsaturated compounds with carbon monoxide and hydrogen in the reaction zone is carried out at a rhodium content of from 2 to 30 ppm, based on the homogeneous reaction mixture.

43. An improved process for preparing aldehydes in a homogeneous organic phase in the presence of at least one rhodium compound and in the absence of complex-forming organophosphorus compounds in this reaction zone by:

a. introduction of an organic solution containing at least one rhodium compound in dissolved form into a reaction zone; and
b. reaction of olefinically unsaturated compounds with carbon monoxide and hydrogen,
wherein the improvement comprises:
addition of at least one organic acid in a total amount, calculated as acid equivalent, of from greater than 3 mol to 3000 mol per mole of rhodium to the rhodium-containing organic solution and subsequent feeding of this solution to the reaction zone, said organic acid being selected from the group consisting of:
(a) n-valeric acid;
(b) 2-methylbutyric acid;
(c) 2-ethylhexanoic acid;
(d) isononanoic acid prepared by hydroformylation of diisobutylene and subsequent oxidation of the hydroformylation product;
(e) isotridecanoic acid prepared by hydroformylation of tetrapropylene and subsequent oxidation of the hydroformylation product;
(f) methanesulphonic acid,
(g) para-toluenesulphonic acid,
(h) benzenesulphonic acid;
(i) benzenedisulphonic acid;
(j) adipic acid and
(k) combinations of any of (a)-(j);
the rhodium content of the rhodium-containing organic solution fed to the reaction zone being from 1000 to 10 000 ppm; the solvent in the organic solution containing at least one rhodium compound in dissolved form being selected from the group consisting of 2-ethylhexanol; isononanol based on 3,5,5-trimethylhexanol and combinations thereof; the reaction of the olefinically unsaturated compounds with carbon monoxide and hydrogen in the reaction zone being carried out at a rhodium content of from 2 to 30 ppm, based on the homogeneous reaction mixture; the reaction of the olefinically unsaturated compounds with carbon monoxide and hydrogen in the reaction zone being carried out at a temperature of from 100 to 150° C., and a pressure of from 0.1 to 30 MPa.

* * * * *